US010004666B2

(12) United States Patent
Berger et al.

(10) Patent No.: US 10,004,666 B2
(45) Date of Patent: Jun. 26, 2018

(54) COMPOSITIONS FOR ENDODONTIC INSTRUMENTS

(71) Applicant: DENTSPLY International Inc., York, PA (US)

(72) Inventors: Todd Berger, Owasso, OK (US); Kevin Wilkinson, Bixby, OK (US); Adam Barantz, Tulsa, OK (US); Dan Ammon, Tulsa, OK (US); Xiaoming Jin, Middletown, DE (US); Bernard Koltisko, Milton, DE (US)

(73) Assignee: DENTSPLY SIRONA Inc., York, PA (US)

( * ) Notice: Subject to any disclaimer, the term of this patent is extended or adjusted under 35 U.S.C. 154(b) by 452 days.

(21) Appl. No.: 14/268,593

(22) Filed: May 2, 2014

(65) Prior Publication Data
US 2014/0335475 A1    Nov. 13, 2014

Related U.S. Application Data

(60) Provisional application No. 61/820,371, filed on May 7, 2013.

(51) Int. Cl.
*A61K 6/08* (2006.01)
*A61K 6/00* (2006.01)
*A61K 6/02* (2006.01)
*A61C 5/55* (2017.01)

(52) U.S. Cl.
CPC .............. *A61K 6/0038* (2013.01); *A61C 5/55* (2017.02); *A61K 6/0091* (2013.01); *A61K 6/024* (2013.01); *A61K 6/0235* (2013.01); *A61K 6/0255* (2013.01)

(58) Field of Classification Search
CPC .................................................. A61K 6/0038
See application file for complete search history.

(56) References Cited

U.S. PATENT DOCUMENTS

| | | |
|---|---|---|
| 4,457,710 A | 7/1984 | McSpadden |
| 4,758,156 A | 7/1988 | Johnson |
| 4,894,011 A | 1/1990 | Johnson |
| 5,118,297 A | 6/1992 | Johnson |
| 5,833,457 A | 11/1998 | Johnson |
| 6,220,863 B1 | 4/2001 | Kamohara et al. |
| 6,472,454 B1 | 10/2002 | Qian |
| 7,168,952 B2 | 1/2007 | Karmaker et al. |
| 7,252,508 B2 | 8/2007 | Karmaker et al. |
| 7,838,573 B2 | 11/2010 | Primus et al. |
| 2005/0066854 A1 | 3/2005 | Jia |
| 2009/0234064 A1 | 9/2009 | Wang et al. |
| 2011/0178234 A1* | 7/2011 | Wang ............... C08C 1/075 524/571 |
| 2011/0230591 A1* | 9/2011 | Berger ............... A61C 5/04 523/117 |

OTHER PUBLICATIONS

Database WPI week 200417 Thomson Scientific, London, GB; AN 2004-171879 XP002728504 & JP 2003192745 A (Kuraray Co Ltd) Jul. 9, 2003 abstract.
Database WPI Week 200417 Thomson Scientific, London, GB: AN 2004-171880, XP002728505, & JP 2003192750 A (Kuraray Co Ltd) Jul. 9, 2003 abstract.
PCT International Search Report PCT/US2014/036612, International Filing Date May 2, 2014, Report dated Aug. 15, 2014.
PCT Written Opinion PCT/US2014/036612, International Filing date May 2, 2014.

* cited by examiner

*Primary Examiner* — Michael Pepitone
(74) *Attorney, Agent, or Firm* — David A. Zdurne; Douglas J. Hura; Leana Levin

(57) ABSTRACT

The present invention is directed to a dental composition, and specifically to an improved composition for endodontic instruments useful for filling root canals or sealing.

13 Claims, No Drawings

COMPOSITIONS FOR ENDODONTIC INSTRUMENTS

CROSS-REFERENCE TO RELATED APPLICATIONS

This patent application claims the benefit of and priority to U.S. Provisional Patent Application Ser. No. 61/820,371, filed on May 7, 2013, which are herein incorporated by reference for all purposes.

FIELD OF THE INVENTION

The present invention is directed to a dental composition, and specifically to an improved composition for endodontic instruments useful for filling root canals or sealing.

BACKGROUND OF THE INVENTION

Previous root canals procedures included a step of sealing the root canal with a sealant material and then a step of filling the sealed root canal with a filling material.

Gutta-percha is the most widely used obturation material. However, gutta-percha does not create a seal. It is a second composition referred to as a sealer which creates the seal and then the two materials work together to prevent bacteria from entering the canal system. The gutta-percha can be improved by heating it above its melt temperature thus allowing it to flow. The melted gutta-percha is compacted with a heated a plugger or a solid carrier. The liquid gutta-percha flows into tubules carrying sealer along with it, thus, creating a more complete seal of the root canal system. However, heated gutta-percha has a very high viscosity and tends to be tacky. So, while it flows, it cannot penetrate all tubules or openings, thus the sealer cannot completely seal the entire system.

Since the sealer will be in the canal system in very thin layers it must be very radiopaque to be seen on the x-ray. Therefore, sealers are typically a reactive composite made up mostly of radiopacifier. If the sealer is to flow to fill the very small gaps to create the seal, the polymer portion of the composite must be a very low viscosity (low molecular weight).

Although these traditional gutta-percha sealer compositions are generally effective in treating root canals, it would be desirable to have a gutta-percha/sealer 2 in 1 composition which could fill the canal system without the need for heat. Ideally, the 2 in 1 composition would have a lower viscosity and be less tacky than melted gutta-percha. This improvement would increase the penetration of the composition into the complex of tubules and tiny openings to more completely seal the entire root canal system. More particularly, the present invention attempts to overcome these deficiencies by providing stable improved 2-in-1 sealer composition (e.g., a sealant composition) and/or adhesion promoter with optional cross-linked formulations and methods for treating root canals using compositions thereof. Desirably, the present invention provides such improved obturation compositions having these desirable properties as well as other beneficial features and advantages,

SUMMARY OF THE INVENTION

The present invention seeks to improve upon prior obturation systems and particularly the filling a tooth root canal by providing an improved sealer, root canal filling material composition, and/or a composite sealant composition. Two types of formulations can be used one as a sealer or one as a root canal filling material. In another aspect, each formulation may be used as a two-in-one sealer and root canal filling material.

In another aspect the root canal filling material flows at room temperature and cures over time. In another aspect, the invention uses liquid GP that polymerizes. In another aspect, the liquid GP reacts in a two-part system where part A reacts with Part B. Of course, one or more of these aspects may be combined to as an alternative formulation of the invention.

Dentin is composed of a collagen (hydrocarbon polymer) matrix holding together crystalline hydroxyapatite (CaP).

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

In general, the present invention is directed to an improved sealant composition and/or a root canal filling material. Advantageously, the sealant composition can be employed to form dental sealants with desirable characteristics. This material enables the preparation of root canals and may be useful for improved bonding (higher adhesion) to the tooth dentin and/or other root canal filling materials. Dental materials containing polymerizable resins and filler particles often are used to prepare the root canals. Such dental materials can be self (chemically)-curable, heat-curable, light-curable, or dual-curable. The dental materials are cured and hardened by different chemical mechanisms to form strong and durable materials for various dental applications. In another aspect the material can be a root canal filling material that cures or polymerizes in-situ. This material enables the preparation of root canals and may be useful for improved bonding (higher adhesion) other root canal filling materials and the dentin. Such dental materials can be self (chemically)-curable, heat-curable, light-curable, or dual-curable. In a third aspect, either the sealer or root canal filling material can act as a two-in-one sealer and root canal filler. This material enables the preparation of root canals and may be useful for improved bonding (higher adhesion) to the tooth dentin and/or other root canal filling materials. Dental materials containing polymerizable resins and filler particles often are used to prepare the root canals. Such dental materials can be self (chemically)-curable, heat-curable, light-curable, or dual-curable. In another aspect of the invention, all of the liquid gutta-percha compositions flow at room temperature producing a room temperature 3D fill and cures over time.

Polymerizable Materials

The polymerizable material (e.g., a composite sealant composition) typically includes at least one polymerizable component and optionally without limitation, one or more of at least one filler (e.g., glass particles), an adhesion promoter, an initiator, a catalyst, an accelerator, an inhibitor, surfactant, mineral trioxide aggregate, radiopacifiers, additive, bioglass, cross-linker or combinations thereof or others.

Polymerizable Compounds

Turning now in greater detail to the individual components of the overall composition. The sealant composition herein may include at least one polymerizable material.

Desirably, the sealant composition may include a liquid polyisoprene (e.g., methacrylated polyisoprene).

The first polymerizable material may typically be present in an amount of at least about 1%, preferably at least about 5%, and more preferable at least about 10% by wt the sealant composition. Furthermore, it is appreciated that the first polymerizable material may typically be present in an amount of less than about 99%, preferably less than about 75% and preferably less than about 50% by wt the overall sealant/root canal filling material composition. For example, the first polymerizable material may typically be present in an amount ranging from about 1% to about 99%, preferably from about 5% to about 75%, and more preferably from about 10% to about 50% by wt the overall composition.

Examples of polymerizable compounds (e.g., liquid polyisoprene copolymers) that may be used in the composition of this invention, include, but are not limited to, cyclic compounds that are capable of undergoing a ring opening reaction such as epoxy modified liquid polyisoprene compounds (e.g., difunctional and multifunctional epoxy silicones) and ring opening nucleophiles such as amine modified liquid polyisoprene compounds (e.g., aminoalkylfunctional liquid Polyisoprene). Most preferred modified liquid polyisoprene are novel. The methacylate polyisoprene can be purchased from Kuraray Co., Ltd.

The first polymerizable material may include a first component (e.g., a cyclic compound that is capable of undergoing a ring opening reaction) and a second component (e.g., ring opening nucleophile) capable of polymerization. For example, the liquid polyisoprene compound may include a first liquid polyisoprene component having an epoxy modified liquid polyisoprene, a second liquid polyisoprene component having an amine modified liquid polyisoprene. The epoxy modified liquid polyisoprene may be present in an amount of at least about 1%, preferably at least about 3%, and more preferable at least about 5% by wt the overall sealant composition. Furthermore, the epoxy modified liquid polyisoprene may be present in an amount of less than about 50%, preferably less than about 40% and preferably less than about 25% by wt the overall sealant composition. For example, the epoxy modified liquid polyisoprene may be present in an amount ranging from about 1% to about 50%, preferably from about 3% to about 40%, and more preferably from about 5% to about 25% by wt the overall sealant composition. An example of the first liquid polyisoprene component having the epoxy modified liquid polyisoprene may be present as formula (I). Further embodiments including the reactive epoxy groups can be placed in several different positions on the polyisoprene molecule.

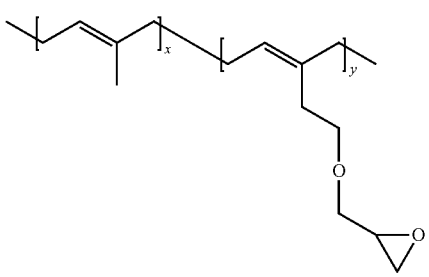

(I)

wherein x is 1-1000, and
y is 1-1000.

Alternatively or in addition to the first liquid polyisoprene component having an epoxy modified liquid polyisoprene. The liquid polyisoprene component may include a second liquid polyisoprene component having an amine modified liquid polyisoprene. The amine modified liquid polyisoprene may be present in an amount of at least about 1%, preferably at least about 3%, and more preferable at least about 5% by wt the overall sealant composition. Furthermore, the amine modified liquid Polyisoprene may be present in an amount of less than about 50%, preferably less than about 40% and preferably less than about 25% by wt the overall sealant composition. For example, the amine modified liquid polyisoprene may be present in an amount ranging from about 1% to about 50%, preferably from about 3% to about 40%, and more preferably from about 5% to about 25% by wt the overall sealant composition.

An example of the second liquid polyisoprene component having the amine modified liquid polyisoprene may be present as in formula (II). Further embodiments including the reactive amine group can placed in several different positions on the polyisoprene molecule

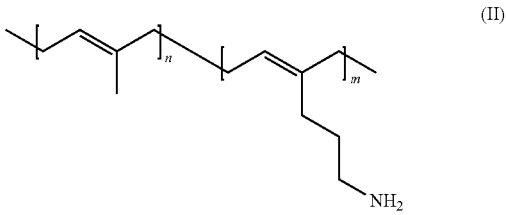

(II)

wherein n is 1-1000, and
m is 1-1000.

Alternatively or in addition to the first liquid polyisoprene component having a modified liquid Polyisoprene containing a free radical polymerization functional group. The free radical polymerization functional group modified liquid polyisoprene may be present in an amount of at least about 1%, preferably at least about 3%, and more preferable at least about 5% by wt the overall sealant composition. Furthermore, the free radical polymerization functional group modified liquid polyisoprene may be present in an amount of less than about 50%, preferably less than about 40% and preferably less than about 25% by wt the overall sealant composition. For example, the free radical polymerization functional group modified liquid polyisoprene (III) may be present in an amount ranging from about 1% to about 50%, preferably from about 3% to about 40%, and more preferably from about 5% to about 25% by wt the overall composition.

An example of the free radical polymerization functional group liquid polyisoprene component having the free radical polymerization functional group modified liquid polyisoprene may be present. In another embodiment, the free radical functionalized polyisoprene contains a different functional group that can react with the disclosed two part systems. Further embodiments including the reactive free radical polymerization functional group can placed in other positions on the polyisoprene molecule and may not include a phenyl group but several different spacer groups.

In one specific embodiment, the first polymerizable material is the polymerizable liquid polyisoprene compound (e.g., 1,3-Butadiene, 2-methyl-,homopolymer, maleated, 2-[(2-methyl-1-oxo-2-propenyl)oxy] ethyl esters) as shown in Formula III.

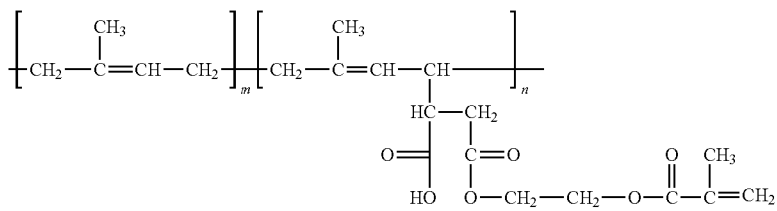

(III)

The liquid polyisoprene may include a molecular weight in an amount of at least about 5,000, preferably at least about 8,000, and more preferable at least about 12,000 g/mol. Furthermore, the liquid polyisoprene may include a molecular weight in an amount of less than about 50,000, preferably less than about 35,000 and preferably less than about 25,000 g/mol. For example, the liquid polyisoprene may include a molecular weight in an amount ranging from about 5,000 to about 50,000, preferably from about 8,000 to about 35,000, and more preferably from about 12,000 to about 25,000 g/mol.

Curing Agent

The composition herein may include at least one initiating component to effectuate curing of the material. The initiating component may be present in an amount of at least about 0.005%, preferably at least about 0.05%, and more preferably at least about 0.05% by wt of the overall composition. The overall composition may include less than about 30%, preferably less than about 20%, and more preferably less than about 15% wt of the initiating component. For example, the initiating component may be present in a range of about 0.005% to about 30%, preferably from about 0.05% to about 20%, and more preferably from about 0.5% to about 15% wt of the overall composition.

Where the composition may be a two part system (Part A and Part B), both Part A and Part B may include at least one initiating component. In one specific example, it is appreciated that the crosslinking reaction may occur through the use of an amine and peroxide, though not required. Optionally, the curing agent may further include an accelerant. One preferred peroxide may include BPO (Luperox® A98, Benzoyl peroxide). Others viable peroxides include, but are not limited to:

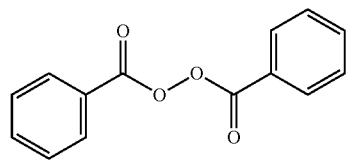

Luperox® A98, Benzoyl peroxide

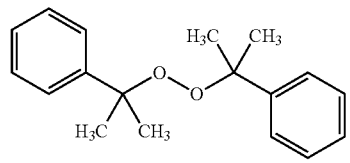

Dicumyl peroxide

-continued

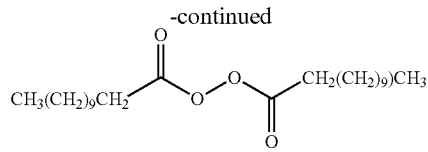

Lauroyl peroxide

One preferred amine may include 2,2'-(4-Methylphenylimino)diethanol (2,2'-(p-Tolylimino)diethanol). Optionally, energy sources such as heat, light (UV and/or IR), or otherwise may be utilized in place of the amine component to effectuate the crosslinking with the peroxide. Others viable amines include, but are not limited to:

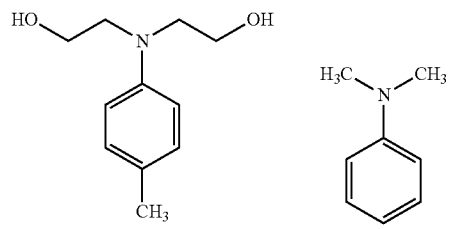

2, 2'-(4-Methylphenylimino)diethanol    n n-dimethylaniline

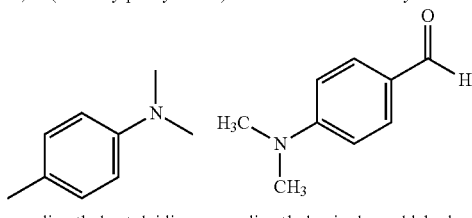

n n-dimethyl-p-toluidine    p-dimethylaminobenzaldehyde

It is believed that the "accelerant" dries the cured surface and over comes oxygen inhibition. One preferred accelerant may include HEMA (2-Hydroxyethyl methacrylate) however, Glycidyl methacrylate (2,3-Epoxypropyl methacrylate) or Lauryl methacrylate (Dodecyl methacrylate) may be viable substitutes for the accelerant as well.

The peroxide component may be present in an amount of at least about 0.05%, preferably at least about 0.5%, and more preferably at least about 1% by wt of the overall composition. The overall composition may include less than about 25%, preferably less than about 20%, and more preferably less than about 15% wt of the peroxide component. For example, the peroxide component may be present in a range of about 0.05% to about 25%, preferably from about 0.5% to about 20%, and more preferably from about 1% to about 15% (e.g., about 1% to about 8%) wt of the overall composition.

The amine component may be present in an amount of at least about 0.005%, preferably at least about 0.05%, and more preferably at least about 0.25% by wt of the overall composition. The overall composition may include less than about 20%, preferably less than about 15%, and more preferably less than about 10% wt of the amine component. For example, the amine component may be present in a range of about 0.005% to about 20%, preferably from about 0.05% to about 15%, and more preferably from about 0.25% to about 10% (e.g., about 0.25% to about 4%) wt of the overall composition.

The accelerant component may be present in an amount of at least about 0.005%, preferably at least about 0.05%, and more preferably at least about 1% by wt of the overall composition. The overall composition may include less than about 25%, preferably less than about 20%, and more preferably less than about 15% wt of the accelerant component. For example, the accelerant component may be present in a range of about 0.005% to about 25%, preferably from about 0.05% to about 20%, and more preferably from about 1% to about 15% (e.g., about 1% to about 10%) wt of the overall composition.

Filler

The composition may include one or more fillers. Fillers having Radiopacity useful in accordance with the invention, without limitation, include inorganic fillers such as Ag, $TiO_2$, $La_2O_3$, $ZrO_2$, $BaSO_4$, $CaWO_4$, $BaWO_4$, $Fe_2O_3$ and $Bi_2O_3$, $CeO_2$, MgO, ZnO, W, $WO_3$, lanthanide salts, polymer granulates, barium or strontium-containing glass. The glass may contain fluoride for fluoride release in vivo. When included, the radiopacifier may be present in an amount of at least about 20%, preferably at least about 30%, and more preferable at least about 40% by wt the overall composition. Furthermore, the radiopacifier may be present in an amount of less than about 80%, preferably less than about 70% and preferably less than about 60% by wt the overall sealant composition. For example, the radiopacifier may be present in an amount ranging from about 20% to about 80%, preferably from about 30% to about 70%, and more preferably from about 40% to about 60% by wt the overall composition. When included, the radiopacifier may present an include at least three radiopacifier materials. In one specific example, the at least three radiopacifiers include from about 20 to about 40% ZrO2, from about 15 to about 35% CaWO4 and from about 1 to about 10% BaSO4.

Other fillers that may be employed include, but are not limited to silicas, aluminas, magnesias, titanias, inorganic salts, metallic oxides, (e.g., zinc oxides, calcium hydroxide, or otherwise), bioglass, mineral trioxide aggregate and glasses, though not required. Other filler material may be present in an amount of at least about 0.1%, preferably at least about 1%, and more preferably at least about 5% by wt the overall sealant composition. Furthermore, the other filler material may be present in an amount of less than about 25%, preferably less than about 20% and more preferably less than about 15% by wt the overall sealant composition. For example, the other filler material may be present in an amount ranging from about 0.1% to about 25%, preferably from about 1% to about 20%, and more preferably from about 5% to about 15% by wt the overall composition.

As shown in Table 1A-1B, two specific examples of the two component sealant composition and/or root canal filler material:

TABLE 1A

| Component A | Weight % | Component B | Weight % |
| --- | --- | --- | --- |
| Liquid Polyisoprene | 20 to 50 | Liquid Polyisoprene | 20 to 50 |
| Peroxide | 0.5 to 20 | Amine | 0.05 to 15 |
| Accelerant | 0.05 to 17 | Accelerant | 0.05 to 17 |
| Radiopacifier | 45 to 75 | Radiopacifier | 45 to 75 |

TABLE 1B

| Component A | Weight % | Component B | Weight % |
| --- | --- | --- | --- |
| Liquid Polyisoprene | 27 to 43 | Liquid Polyisoprene | 27 to 43 |
| Peroxide | 1 to 10 | Amine | 0.5 to 5 |
| Accelerant | 0.5 to 7 | Accelerant | 0.5 to 7 |
| Radiopacifier | 51 to 67 | Radiopacifier | 51 to 67 |

The composition may further include additives, pharmaceutical active ingredients, dyes or pigments (e.g., iron oxides) waxes, oils (e.g., silicone oil and paraffin oil), surfactants, fatty acids (e.g., stearic acid), anti-oxidants, preservatives (e.g., nanosilver), or mixtures thereof.

Optionally, the composition may further include a cross-linked material (e.g., cross-linked rubber such as polyisoprene or otherwise). One example of a cross-linked material may include a cross-linked cis-1,4-polyisoprene-based material. As shown in Tables 2 and 3, the cross-linked material may include the following compositions as described in U.S. Ser. No. 13/045744, filed Mar. 11, 2011, which is herein incorporated by reference for all purposes

TABLE 2

| Component | Weight % |
| --- | --- |
| 1-4,Polyisoprene | 10 to 40 (e.g., 20 to 35) |
| Curing Agent | 0.1 to 30 (e.g., 5 to 15) |
| Curing Co agent | 0.0 to 30 |
| Zinc Oxide | 0 to 80 |
| Radiopacifier | 30 to 85 (e.g., 50 to 70) |
| Reinforcing Fillers | 0 to 50 |
| Carbon Nanotubes | 0 to 50 |
| Fibers | 0 to 50 |
| Colorant | 0 to 10 |

TABLE 3

| Component | Weight % |
| --- | --- |
| Cross-Linkable Material | 10 to 40 |
| Rubber | 0.5 to 15 |
| Curing Agent | 0.1 to 30 |
| Curing Co agent | 0.0 to 15 |
| Antimicrobial | 0.01 to 50 |
| Radiopacifier | 20 to 75 |
| Reinforcing Fillers | 0.5 to 30 |
| Fibers | 0.5 to 30 |
| Colorant | 0.01 to 25 |
| Anti Oxidant | 0 to 10 |
| Processing Aid | 0 to 10 |

When included, the cross-linked material may be present in an amount of at least about 3%, preferably at least about 5%, and more preferably at least about 10% by wt the overall sealant composition. Furthermore, the cross-linked material may be present in an amount of less than about 50%, preferably less than about 40% and more preferably less than about 30% by wt the overall sealant composition. For example, the cross-linked material may be present in an amount ranging from about 3% to about 50%, preferably from about 5% to about 40%, and more preferably from about 10% to about 30% by wt the overall composition.

The cross-linked material may be provided as a powder (e.g., from a grinding or chopping process of the cross-linked material). The cross-linked material may include a particle size of at least about 5 microns, preferably at least about 10 microns and more preferably at least about 25 microns. Furthermore, the cross-linked material may include a particle size of less than about 500 microns, preferably less than about 400 microns, and more preferably less than about 300 microns. For example, the cross-linked material may include a particle size ranging from about 5 to about 500 microns, preferably from about 10 to about 300, and more preferably from about 25 to about 350 microns (e.g., from about 50 microns to about 100 microns or from about 125 microns to about 200 microns).

Adhesion Promoter

The composition may further include at least one adhesion promoter. In one aspect, the adhesion promoter (e.g., second polymerizable material) may be present in addition to the polymerizable compound (e.g., second polymerizable material). In another aspect the adhesion promoter may be the polymerizable compound.

Without intending to be bound by theory, it is believed that the adhesion promoter herein makes advantageous employment of a particular molecularstructure by which at least a portion of the molecule may include cyclic compounds that are capable of undergoing a ring opening reaction functionality (e.g., epoxy group, a succunic anhydride group, a succinimide group, or otherwise) and/or ring opening nucleophile functionality (e.g., OH, COOH, SH amine group, such as diepoxide or diamine group, or otherwise), which is capable of cross-linking the sealant composition. The adhesion promoter molecular structure may include hydrophobic functionality such as a hydrocarbon, a silicone (e.g., it is silanated such as SiO, SiO$_2$, SiH$_4$, or SiC), or otherwise, which is capable of being a thickener and/or may be provided as a dispersion carrier for the cross-linked material discussed herein. Furthermore, the adhesion promoter molecular structure may include a dentin binding functionality, such as an phosphate, sulfate, sulfonate, betaine, carboxylic acids, amino acid, diacids, bisphosphate, or phosphatidylcholine functionality, which is capable of improving the linkage with the tooth dentin such as through the molecular network of the composition.

The adhesion promoter may be a one component material or a two component material. Examples of the adhesion promoter include but are not limited to:

i)

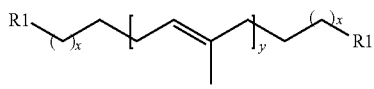

wherein

R1 is independently a ring opening nucleophile such as NH$_2$, OH, COOH, SH or otherwise, whereas R$^1$ may be identical or different;

x is an integer from 0 to 10 (e.g., 1 to 10); and y is an integer of from 1 to 1000.

ii)

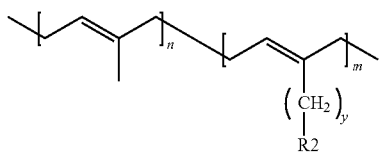

wherein

R$^2$ is independently NH$_2$, OH, COOH, SH, an epoxide, a succunic anhydride, or a succinimide group, whereas multiple groups of R$^2$ may be identical or different, (preferably R$^2$ is a ring opening nucleophile such as NH$_2$, OH, COON, SH or otherwise);

y is an integer of from 1 to 10, multiple groups of y may be identical or different;

n is an integer of from 1 to 1000 (e.g., 1 to 100, preferably 1 to 10), multiple groups of n may be identical or different; and m is an integer of from 0 to 1000 (e.g., 1 to 100, preferably 45 to 65), multiple groups of m may be identical or different.

iii)

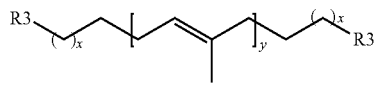

wherein

R$^3$ is independently a cylic compound that may undergo ring polymerization such as an epoxide, a succunic anhydride, a succinimide group, or otherwise, whereas R$^3$ may be identical or different;

x is an integer of from 0 to 10 (e.g., 1 to 10); and y is an integer of from 1 to 1000.

iv)

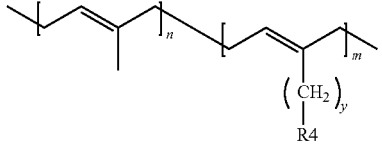

wherein

R$^4$ is independently a cyclic compound that may undergo ring polymerization such as an epoxide, a succunic anhydride, a succinimide group, or otherwise, whereas multiple groups of R$^4$ may be identical or different;

y is an integer of from 1 to 10;

n is an integer of from 1 to 1000; and m is an integer of from 0 to 1000 (e.g., 1 to 1000), multiple groups of m may be identical or different.

v)

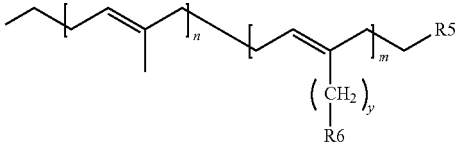

wherein

R$^5$ is independently NH$_2$, OH, COON, SH, an epoxide, a succunic anhydride, or a succinimide group, whereas multiple groups of R$^5$ may be identical or different;

R$^6$ is independently a phosphate, a sulfate, a sulfonate, a betaine, a carboxylic acid, an amino acid, a diacids, a bisphosphate, or a phosphatidylcholine group, whereas multiple groups of R$^6$ may be identical or different;

y is an integer of from 1 to 10, multiple groups of y may be identical or different;

n is an integer of from 1 to 1000, multiple groups of n may be identical or different; and m is an integer of from 0 to 1000 (e.g., 1 to 1000), multiple groups of m may be identical or different; and wherein $R^5$ and $R^6$ can change positions.

The adhesion promoter may be a one component material or a two component material. Examples of the adhesion promoter include but are not limited to:

vi)

[Chemical structure showing a polymer with repeating units labeled A, B, C with R9(—)y and R10(—)z substituents]

wherein $R^9$ is independently $NH_2$, OH, COOH, SH, an epoxide, a succunic anhydride, or a succinimide group, whereas multiple groups of $R^9$ may be identical or different;

$R^{10}$ is independently a phosphate, a sulfate, a sulfonate, a betaine, a carboxylic acid, an amino acid, a diacids, a bisphosphate, or a phosphatidylcholine group, whereas multiple groups of $R^{10}$ may be identical or different;

y is an integer of from 1 to 10, multiple groups of y may be identical or different;

z is an integer of from 1 to 10, multiple groups of z may be identical or different;

A is an integer of from 1 to 1000, multiple groups of A may be identical or different; and B is an integer of from 1 to 1000, multiple groups of B may be identical or different; and C is an integer of from 0 to 1000 (e.g., 1 to 1000), multiple groups of C may be identical or different; and wherein $R^9$ and $R^{10}$ can change positions.

In one embodiment, each functional portion is present thereby forming a ter-polymer adhesion promoter.

vii)

[Chemical structure showing a ter-polymer with three repeating units labeled n, m, p with ester linkages to R13, R14, R15 substituents]

wherein $R^{13}$ is independently a phosphate, a sulfate, a sulfonate, a betaine, a carboxylic acid, an amino acid, a diacids, a bisphosphate, or a phosphatidylcholine group, whereas multiple groups of $R^{13}$ may be identical or different;

$R^{14}$ is independently a hydrophobic group such as a hydrocarbon, a silicone (e.g., it is silanated), or otherwise, (preferably the silicone includes a Tris(trimethylsiloxy)silyl group such as [tris(trimethylsilyloxy)silyl]propyl methacrylate), whereas multiple groups of $R^{14}$ may be identical or different;

$R^{15}$ is independently $NH_2$, OH, COOH, SH, an epoxide, a succunic anhydride, or a succinimide group, whereas multiple groups of $R^{15}$ may be identical or different;

n is an integer of from 1 to 1000, multiple groups of x may be identical or different;

m is an integer of from 0 to 1000 (e.g., 1 to 1000), multiple groups of y may be identical or different;

p is an integer of from 1 to 1000, multiple groups of z may be identical or different; and wherein $R^{13}$, $R^{14}$, and $R^{15}$ can change positions.

It is appreciated that a two component adhesion promoter may include a first component of the formula i)-vii) having a cyclic compound that may undergo ring polymerization such as an epoxide, a succunic anhydride, a succinimide group, or otherwise and a second component of the formula i)-vii) having a ring opening nucleophile such as $NH_2$, OH, COOH, SH or otherwise. When included, polymerization may occur by mixing the first and second components to form the adhesion promoter.

The adhesion promoter may be synthesized by various processes. Desirably, the ter-polymer adhesion promoter may be formed by RAFT polymerization to form a two component system. For example, the first component (having a cyclic compound that may undergo ring polymerization) may be formed by the following RAFT polymerization:

[Chemical structure of Ethylene glycol methacrylate phosphate (EGMP)]

Ethylene glycol methacrylate phosphate (EGMP)

[Chemical structure of TRIS-methacrylate (TRIS-MA)]

TRIS-methacrylate (TRIS-MA)

→ RAFT Polymerization

[Chemical structure of Glycidyl methacrylate (GMA)]

Glycidyl methacrylate (GMA)

[Chemical structure of resulting ter-polymer Adhesion Promoter with n, m, p repeating units]

Adhesion Promoter

The second component (having a ring opening nucleophile) may be formed by the following RAFT polymerization:

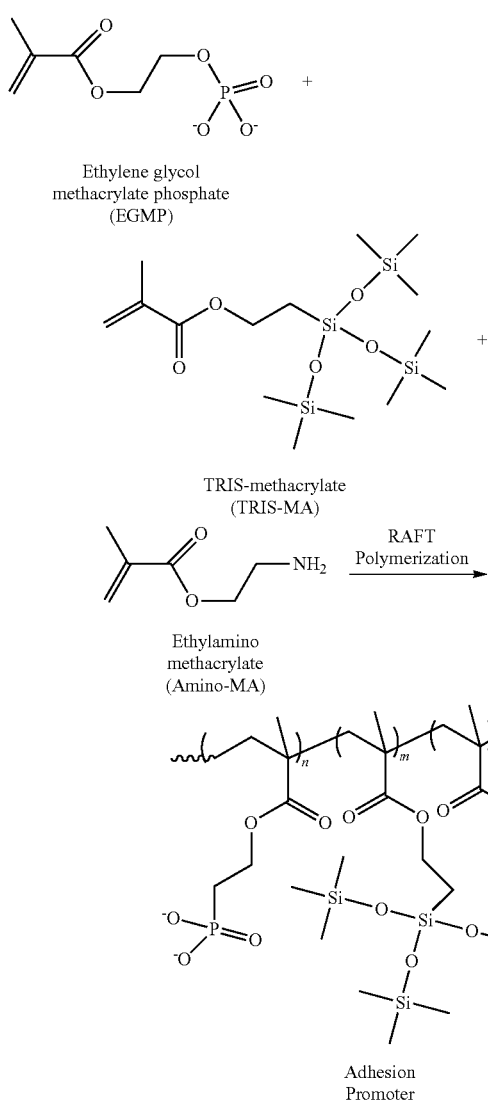

Ethylene glycol methacrylate phosphate (EGMP)

TRIS-methacrylate (TRIS-MA)

Ethylamino methacrylate (Amino-MA)

RAFT Polymerization

Adhesion Promoter

These specific examples i)-vii) of possible adhesion promoters should not be construed as limiting examples.

The adhesion promoter may be present in an amount of at least about 3%, preferably at least about 5%, and more preferably at least about 10% by wt the overall composition. Furthermore, the adhesion promoter may be present in an amount of less than about 50%, preferably less than about 40% and more preferably less than about 30% by wt the overall sealant composition. For example, the adhesion promoter may be present in an amount ranging from about 3% to about 50%, preferably from about 5% to about 40%, and more preferably from about 10% to about 30% by wt the overall composition.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. An endodontic root canal filling material or sealant composition for filling and sealing a root canal comprising at least two separate materials including:
   a first material having:
      (i) polymerizable liquid gutta-percha being liquid polyisoprene, wherein the liquid polyisoprene is present in an amount of 20-50% by wt. of the composition; and
      (ii) a peroxide component; and
   a second material having:
      (i) a liquid polyisoprene; and
      (ii) an amine component;
   wherein the first material, the second material or both include a radiopacifier, the radiopacifier being present in an amount of 45-75% by wt. of the composition.

2. The composition according to claim 1, wherein the liquid gutta percha includes methacrylated polyisoprene.

3. The composition according to claim 1, wherein the peroxide is selected from the group consisting of benzoyl peroxide, dicumyl peroxide, lauroyl peroxide, and mixtures thereof.

4. The composition according to claim 1, wherein the first material, the second material or both further comprise an adhesion promoter selected from the group consisting of:

i)

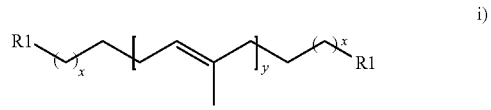

wherein
R1 is independently a ring opening nucleophile, whereas R1 may be identical or different;
x is an integer from 0 to 10; and
y is an integer of from 1 to 1000,

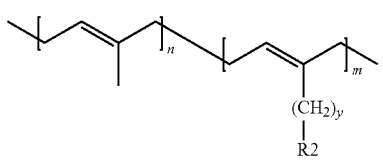

ii)

wherein
R2 is independently NH$_2$, OH, COOH, SH, an epoxide, a succunic anhydride, or a succinimide group, whereas multiple groups of R2 may be identical or different;
y is an integer of from 1 to 10, multiple groups of y may be identical or different;
n is an integer of from 1 to 1000, multiple groups of n may be identical or different; and
m is an integer of from 0 to 1000, multiple groups of m may be identical or different,

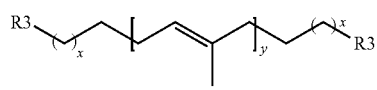

iii)

wherein
R3 is independently a cylic compound that may undergo ring polymerization, whereas R3 may be identical or different;
x is an integer of from 0 to 10; and
y is an integer of from 1 to 1000,

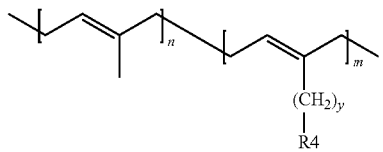

iv)

wherein
R4 is independently a cyclic compound that may undergo ring polymerization, whereas multiple groups of R4 may be identical or different;
y is an integer of from 1 to 10;
n is an integer of from 1 to 1000; and
m is an integer of from 0 to 1000, multiple groups of m may be identical or different,

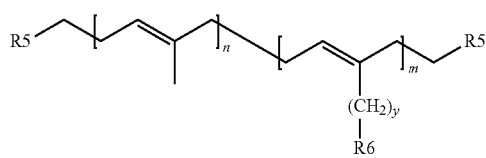

v)

wherein
R5 is independently NH$_2$, OH, COOH, SH, an epoxide, a succunic anhydride, or a succinimide group, whereas multiple groups of R5 may be identical or different;
R6 is independently a phosphate, a sulfate, a sulfonate, a betaine, a carboxylic acid, an amino acid, a diacids, a bisphosphate, or a phosphatidylcholine group, whereas multiple groups of R6 may be identical or different;
y is an integer of from 1 to 10, multiple groups of y may be identical or different;
n is an integer of from 1 to 1000, multiple groups of n may be identical or different; and
m is an integer of from 0 to 1000, multiple groups of m may be identical or different; and
wherein R5 and R6 can change positions;

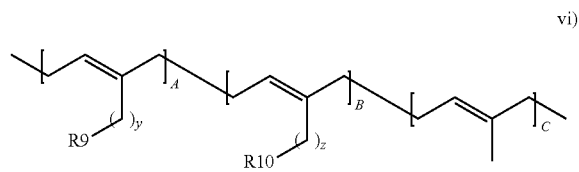

vi)

wherein
R9 is independently NH$_2$, OH, COOH, SH, an epoxide, a succunic anhydride, or a succinimide group, whereas multiple groups of R9 may be identical or different;
R10 is independently a phosphate, a sulfate, a sulfonate, a betaine, a carboxylic acid, an amino acid, a diacids, a bisphosphate, or a phosphatidylcholine group, whereas multiple groups of R10 may be identical or different;
y is an integer of from 1 to 10, multiple groups of y may be identical or different;
z is an integer of from 1 to 10, multiple groups of z may be identical or different;
A is an integer of from 1 to 1000, multiple groups of A may be identical or different; and
B is an integer of from 1 to 1000, multiple groups of B may be identical or different; and
C is an integer of from 0 to 1000, multiple groups of C may be identical or different; and
wherein R9 and R10 can change positions,

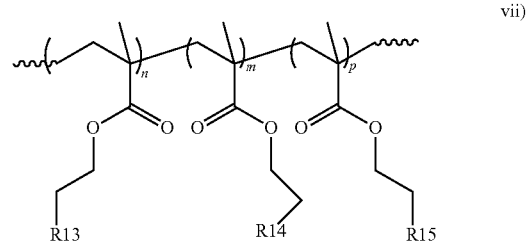

vii)

wherein
R13 is independently a phosphate, a sulfate, a sulfonate, a betaine, a carboxylic acid, an amino acid, a diacids, a bisphosphate, or a phosphatidylcholine group, whereas multiple groups of R13 may be identical or different;
R14 is independently a hydrophobic group, whereas multiple groups of R14 may be identical or different;
R15 is independently NH$_2$, OH, COOH, SH, an epoxide, a succunic anhydride, or a succinimide group, whereas multiple groups of R15 may be identical or different;
n is an integer of from 1 to 1000, multiple groups of x may be identical or different;
m is an integer of from 0 to 1000, multiple groups of y may be identical or different;

p is an integer of from 1 to 1000, multiple groups of z may be identical or different; and wherein R9, R14, and R15 can change positions, and viii) mixtures thereof.

5. The composition of claim 4, wherein R1 is selected from the group consisting of $NH_2$, OH, COOH, SH and mixtures thereof;

wherein R3 is selected from the group consisting of an epoxide, a succunic anhydride, a succinimide group, and mixture thereof;

wherein R4 is selected from the group consisting of an epoxide, a succunic anhydride, a succinimide group, and mixtures thereof; or wherein R14 is selected from the group consisting of a hydrocarbon, a silicone, and mixture thereof.

6. The composition according to claim 1, further comprising less than about 70% by weight of the overall composition of a cross-linked cis-polyisoprene.

7. The composition according to claim 1, wherein the radiopacifier is selected from the group consisting of tungsten, zinc, zinc oxide, tungsten oxide, barium, barium sulfate, bismuth, bismuth oxide, zirconium oxide, and calcium tungstate.

8. An endodontic root canal filling material or sealant composition for filling and sealing a root canal comprising at least two separate materials including:
   a first material having:
      (i) polymerizable liquid gutta-percha being liquid polyisoprene; and
      (ii) a peroxide component; and
   a second material having:
      (i) a liquid polyisoprene; and
      (ii) an amine component;
   wherein the amine is selected from the group consisting of 2,2'-(4-Methylphenylimino)diethonal, n,n-dimethylaniline, n,n-dimethyl-p-toluidine, p-dimethylaminobenzaldehyde, and mixtures thereof.

9. The composition of claim 8, wherein the first material, the second material or both further comprise a filler.

10. The composition according to claim 9, wherein the filler is selected for the group consisting of a polymer, silica, crosslinked-cis-polyisoprene microparticles, fumed silica, bioglass, mineral trioxide aggregate, and any combination thereof.

11. The composition according to claim 8, wherein the first material, the second material or both further include an accelerant selected from the group consisting of HEMA (2-Hydroxyethyl methacrylate), Glycidyl methacrylate (2,3-Epoxypropyl methacrylate), Lauryl methacrylate (Dodecyl methacrylate) and mixtures thereof.

12. The composition according to claim 11, wherein 0.05 to 17% of the accelerant is present.

13. An endodontic root canal filling material or sealant composition for filling and sealing a root canal comprising at least two separate materials including:
   a first material having:
      (i) polymerizable liquid gutta-percha being liquid polyisoprene; and
      (ii) a peroxide component; and
   a second material having:
      (i) a liquid polyisoprene; and
      (ii) an amine component;
   wherein the first material, the second material, or both further include bioglass or a bioactive glass.

* * * * *